United States Patent
Garcon et al.

(10) Patent No.: US 9,138,471 B2
(45) Date of Patent: *Sep. 22, 2015

(54) METHODS FOR ONE-DOSE INTRADERMAL DELIVERY FOR NON-LIVE TRIVALENT INFLUENZA VACCINE

(75) Inventors: Nathalie Garcon, Rixensart (BE); Moncef Mohamed Slaoui, Rixensart (BE); Christian Van Hoecke, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/271,839

(22) Filed: Oct. 12, 2011

(65) Prior Publication Data

US 2012/0039933 A1   Feb. 16, 2012

Related U.S. Application Data

(63) Continuation of application No. 11/762,488, filed on Jun. 13, 2007, now Pat. No. 8,557,251, which is a continuation of application No. 10/469,191, filed as application No. PCT/EP02/01844 on Feb. 21, 2002, now abandoned.

(30) Foreign Application Priority Data

Feb. 23, 2001 (GB) .................................. 0104538.4
Mar. 26, 2001 (GB) .................................. 0107511.8
Apr. 3, 2001 (GB) .................................. 0108365.8

(51) Int. Cl.
*A61K 39/145* (2006.01)
*A61K 39/00* (2006.01)

(52) U.S. Cl.
CPC ....... *A61K 39/145* (2013.01); *A61K 2039/5252* (2013.01); *A61K 2039/54* (2013.01); *C12N 2760/16134* (2013.01); *C12N 2760/16234* (2013.01)

(58) Field of Classification Search
CPC ............. A61K 2039/54; A61K 39/145; C12N 2760/16134; C12N 2760/16234
See application file for complete search history.

(56) References Cited

U.S. PATENT DOCUMENTS 5,141,496 A      8/1992   Dalto et al.
8,465,468 B1     6/2013   Pettis et al.
8,557,251 B2 *  10/2013   Garcon et al. ............. 424/209.1

FOREIGN PATENT DOCUMENTS

IL           84811         2/1993
WO      WO 96/33739    * 10/1996  ............. A61K 39/39

OTHER PUBLICATIONS

Majeski (2004) Duluth News-Tribune Oct. 27 Two doctors recommend way to stretch flu vaccine p. 1-2.*
du Chatelet et al (Vaccine 15:449-549, 1997).*
Sanofi Pasteur 314 and 329—Vaxigrip® Product Monograph, p. 1-25. Jun. 4, 2008.*
Beyer et al., Comparison of Serology and Reactogenicity between Influenza Subunit Vaccines and Whole Virus of Split Vaccines, Clinical Drug Invest., Clinical Use, Jan. 1998, vol. 15, No. 1, pp. 1-12.
Jakob et al., Epidermal Langerhans Cells: From Neurona to Natures Adjuvants, Advances in Dermatology, 1999, vol. 14, pp. 209-259.
Steinman, et al., Exploiting Dendritic Cells to Improve Vaccine Efficacy, The Journal of Clinical Investigation, 2002, vol. 109, No. 12, pp. 1519-1526.
Kunzel, et al., Immune Response to Influenza Vaccination, Lancet, Jan. 15, 1996, vol. 343, pp. 173.
Kunzel, et al., Kinetics of Humoral antibody response to Trivalent Inactivated Split Influenza Vaccine in Subjects Previously vaccinated of Vaccinated for the first time, Vaccine, vol. 14, No. 12, pp. 1108-1110, 1996.
Saslaw et al., "Antibody Response to Polyvalent Influenza Virus Vaccine Administered Intradermally of Subcutaneously in an Aged Population", The Americal Journal of The Medical Sciences, Apr. 1963, pp. 1-12.

* cited by examiner

*Primary Examiner* — Mary E Mosher
(74) *Attorney, Agent, or Firm* — Michael M. Conger

(57) ABSTRACT

The invention relates to methods for one-dose influenza vaccine for intradermal delivery of a trivalent, non-live influenza antigen preparation, particularly a split influenza preparation.

20 Claims, 1 Drawing Sheet

*Anti-Influenza Immunoglobulin Titers in Primed Pigs Following IM or ID Vaccination with Fluarix*[TM]
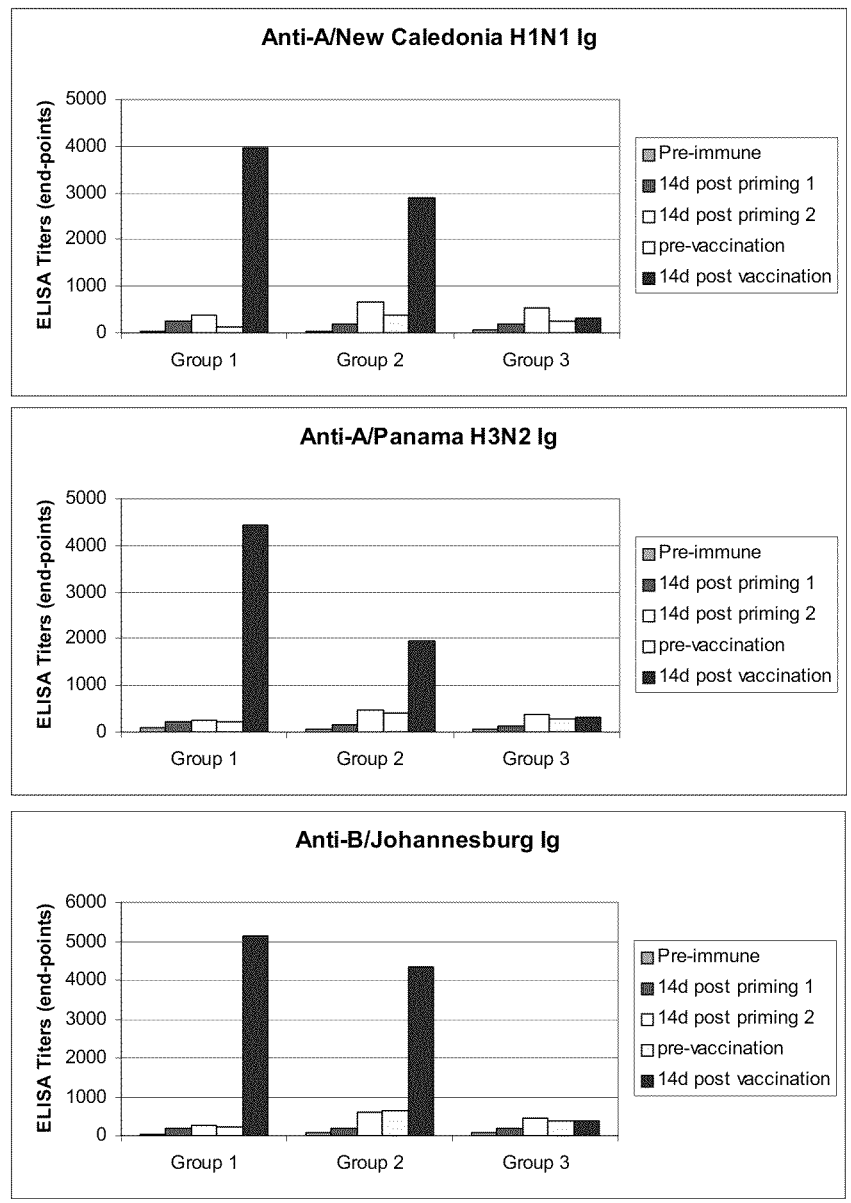

METHODS FOR ONE-DOSE INTRADERMAL DELIVERY FOR NON-LIVE TRIVALENT INFLUENZA VACCINE

CROSS-REFERENCE TO RELATED APPLICATIONS

This application is a continuation application of the U.S. application Ser. No. 11/762,488, filed 13 Jun. 2007, which is a continuation application of U.S. application Ser. No. 10/468,191 filed 25 Aug. 2003, now abandoned, which was a 371 of International Application No. PCT/EP02/01844, filed 21 Feb. 2002, which claims priority to GB 0108365.8 filed 3 Apr. 2001, GB0107511.8 filed 26 Mar. 2001 and GB0104538.4, filed 23 Feb. 2001, the contents of all of which are herein incorporated by reference in their entirety.

FIELD OF THE INVENTION

This invention relates to influenza vaccine formulations for intradermal delivery, methods for preparing them and their use in prophylaxis or therapy. More particularly the invention relates to the use of influenza vaccines which can be administered intradermally in a single dose to achieve a sufficient immune response to meet regulatory requirements.

BACKGROUND OF THE INVENTION

Influenza virus is one of the most ubiquitous viruses present in the world, affecting both humans and livestock. The economic impact of influenza is significant.

SUMMARY OF THE INVENTION

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of the host-derived lipid material. The surface glycoproteins neuraminidase (NA) and haemagglutinin (HA) appear as spikes, 10 to 12 nm long, at the surface of the particles. It is these surface proteins, particularly the haemagglutinin, that determine the antigenic specificity of the influenza subtypes.

DESCRIPTION OF THE FIGURE

FIG. 1 shows three bar graphs of anti-influenza immunoglobulin titers in primed pigs following intramuscular or intradermal vaccination with Fluarix™.

DETAILED DESCRIPTION OF THE INVENTION

Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease. These groups in particular therefore need to be protected.

Currently available influenza vaccines are either inactivated or live attenuated influenza vaccines. Inactivated flu vaccines comprise one of three types of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are generally given intramuscularly (i.m.).

Influenza vaccines, of all kinds, are usually trivalent vaccines. They generally contain antigens derived from two influenza A virus strains and one influenza B strain. A standard 0.5 ml injectable dose in most cases contains 15 mg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330).

In certain circumstances, such as the occurrence of a pandemic influenza strain, it may be desirable to have a vaccine which contains only the single strain. This will help the speed of response to a pandemic situation.

The influenza virus strains to be incorporated into influenza vaccine each season are determined by the World Health Organisation in collaboration with national health authorities and vaccine manufacturers.

Current efforts to control the morbidity and mortality associated with yearly epidemics of influenza are based on the use of intramuscularly administered inactivated influenza vaccines. The efficacy of such vaccines in preventing respiratory disease and influenza complications ranges from 75% in healthy adults to less than 50% in the elderly.

It would be desirable to provide an alternative way of administering influenza vaccines, in particular a way that is pain-free or less painful than i.m. injection, and does not involve the associated negative affect on patient compliance because of "needle fear". It would also be desirable to target the cell mediated immune system for example by targeting the antigen to the dendritic cells and langerhans cells that reside in the skin, particularly in the dermis. Cell mediated immunity appears to assist with viral clearance and recovery from illness and may provide better cross protection between influenza strains than antibodies. It has also been described in the literature that intradermal administration allows for the induction of a mucosal immunity at the level of the mucosal surfaces. This offers a benefit compared to the parenteral route for a vaccine against a pathogen such as influenza where the portal of entry of the virus is through the nasal route. Thus the mucosal surfaces, initially in the upper respiratory tract, offer the first line of defence.

Furthermore, it would be desirable to reduce the amount of antigen needed for a dose of influenza vaccine. Influenza vaccines are often in short supply.

Experimental intradermal exposure of humans to inactivated influenza vaccines dates back as far as the 1940s. Although the benefits of intradermal vaccination have long been recognised, there has to date been no consensus view that regular vaccination for influenza would be effective and practicable via the intradermal route.

Crowe (1965) Am J Medical Technology 31, 387-396 describes a study comparing intradermal and subcutaneous vaccination with a split influenza vaccine. Two doses of 0.1 ml of vaccine were administered intradermally, 14 days apart. The results obtained for intradermal delivery did not meet the standards set for two of the three strains tested, either after one or after two doses.

McElroy (1969) in New Eng J of Medicine, 6 November, page 1076 describes the administration of a monovalent A strain vaccine intradermally in two doses and suggests that the intradermal route might be considered when vaccine is scarce e.g. when a new, unexpected strain arises.

Tauraso et al (1969) Bull Wld Hlth Org 41, 507-516 describe a study using monovalent, whole inactivated influenza vaccine administered subcutaneously (0.25 ml or 0.5 ml) or intradermally (0.1 ml). A booster inoculation was given. The results suggest intradermal delivery is a reasonable alternative to subcutaneous delivery, but the authors suggest that two doses are necessary.

Foy (1970) in a letter to JAMA, Jul. 6, 1970, vol 213 page 130, discusses an experiment to test intradermally administered flu vaccine under natural challenge. Two doses of vaccine were given, three to four weeks apart. The data apparently suggested that intradermal vaccination did prevent disease, but were not conclusive.

In a letter to the British Medical Journal, Oct. 29, 1977 page 1152, an experiment using a jet gun to deliver 0.15 ml of monovalent influenza vaccine intradermally was described with unfavourable results. Intradermal administration was described as requiring further work.

Other authors have pointed out that intradermal injection carries with it the risk of leakage, as does subcutaneous injection. However, because of the small volume of vaccine used in intradermal administration, leakage might result in little or no protection being conferred.

Brooks et al (1977) Annals of Allergy 39, 110-112 describe a study in which killed influenza vaccine containing two A strains (40 CCA units of each) and separately a B strain (100 CCA units) was administered intradermally in a 0.1 ml volume. The authors concluded that the intradermal route was feasible and effective for immunisation but that larger doses than can be given intradermally may be required for certain strains.

Brown et al (1977) J Infectious Disease 136, 466-471 describe intradermal administration of a formalin-inactivated, whole monovalent influenza A strain vaccine. 40 CCA were used in a 0.1 ml volume. This was compared to intramuscular administration of 0.5 ml (200 CCA). The response to intradermal vaccination was found to be age-dependent and lower than for i.m. vaccination for those with preexisting antibody. The conclusion was that with the vaccination doses used in this study, intradermal vaccination should only be used in special circumstances.

Halperin et al (1979) AJPH 89, 1247-1252 describe a comparison of intradermal and subcutaneous routes of influenza vaccination with a bivalent split virus vaccine. 0.1 ml of vaccine containing 40 CCA of each strain was used for the i.d. vaccination.

Herbert and Larke (1979) J Infectious Diseases 140, 234-238 describe a comparison of intradermal and subcutaneous influenza vaccination using a bivalent whole virus vaccine. The intradermal route was found to be less effective than the subcutaneous route where there was little or no previous exposure to the vaccine strain. The authors also observed no advantage in the smaller antigenic mass of the intradermal inoculum in relation to reactogenicity, since this did not appear to reduce side effects from the vaccine that occur with the higher dose subcutaneous immunisation.

Bader (1980) in a letter to AJPH, vol. 70 no. 5 discusses the results of various trials with intradermal delivery of flu vaccine and supports the potential value of intradermal delivery when two doses are given two weeks apart.

Niculescu et al (1981) in Arch Roum Path Exp Microbiol, 40, 67-70 describe intradermal administration of a split trivalent vaccine using a "gun-jet injector". Two doses were given, one month apart. The authors conclude that this method of administration can be used to decrease the rate of disease during influenza epidemics.

Thus, the literature shows an interest in intradermal vaccination between the mid-sixties (or earlier) and the early 1980s. However, the prevailing view appears to have been that two doses of vaccine would be needed. Also, there was a widely held view that due to the difficulty of administration and the lack of certainty that the low volume of vaccine would successfully be located in the desired region, the use of the intradermal delivery route would be considered only when rapid and mass vaccination was required e.g. in response to a widespread epidemic. Interestingly, there is little mention of intradermal flu vaccination in the literature since the early eighties. Since the early eighties there has been little mention of intradermal flu vaccination using a protein antigen approach in the literature. Protein efforts appear to have fallen out of favour and attention was turned instead to DNA vaccination. See review by Webster R. G. (1999) in Clin Infect Dis, 28, 225-229 and publications such as Degano et al (1999) Vaccine 18, 623-32; Haensler et al (1999) Vaccine 17, 628-638; Degano et al (1998) Vaccine 16, 394-398.

Thus, the commercially available influenza vaccines remain the intramuscularly administered split or subunit intramuscular vaccines. These vaccines are prepared by disrupting the virus particle, generally with an organic solvent or a detergent, and separating or purifying the viral proteins to varying extents. Split vaccines are prepared by fragmentation of whole influenza virus, either infectious or inactivated, with solubilizing concentrations of organic solvents or detergents and subsequent removal of the solubilizing agent and some or most of the viral lipid material. Split vaccines generally contain contaminating matrix protein and nucleoprotein and sometimes lipid, as well as the membrane envelope proteins. Split vaccines will usually contain most or all of the virus structural proteins although not necessarily in the same proportions as they occur in the whole virus. Subunit vaccines on the other hand consist essentially of highly purified viral surface proteins, haemagglutinin and neuraminidase, which are the surface proteins responsible for eliciting the desired virus neutralising antibodies upon vaccination. Matrix and nucleoproteins are either not detectable or barely detectable in subunit vaccines.

Standards are applied internationally to measure the efficacy of influenza vaccines. The European Union official criteria for an effective vaccine against influenza are set out in the table below. Theoretically, to meet the European Union requirements, an influenza vaccine has to meet only one of the criteria in the table, for all strains of influenza included in the vaccine. However in practice, at least two or more probably all three of the criteria will need to be met for all strains, particularly for a new vaccine such as a new intradermal vaccine. Under some circumstances two criteria may be sufficient. For example, it may be acceptable for two of the three criteria to be met by all strains while the third criterion is met by some but not all strains (e.g. two out of three strains). The requirements are different for adult populations (18-60 years) and elderly populations (>60 years):

|  | 18-60 years | >60 years |
| --- | --- | --- |
| Seroconversion rate* | >40% | >30% |
| Conversion factor** | >2.5 | >2.0 |
| Protection rate*** | >70% | >60% |

*Seroconversion rate is defined as the percentage of vaccinees who have at least a 4-fold increase in serum haemagglutinin inhibition (HI) titres after vaccination, for each vaccine strain.
**Conversion factor is defined as the fold increase in serum HI geometric mean titres (GMTs) after vaccination, for each vaccine strain.
***Protection rate is defined as the percentage of vaccinees with a serum HI titre equal to or greater than 1:40 after vaccination (for each vaccine strain) and is normally accepted as indicating protection.

For an intradermal flu vaccine to be commercially useful it will not only need to meet those standards, but also in practice it will need to be at least as efficacious as the currently available intramuscular vaccines. It will also need to be produced by an acceptable process and will of course need to be commercially viable in terms of the amount of antigen and the number of administrations required. Furthermore, it will need to be administered using a procedure which is reliable and straightforward for medical staff to carry out.

Although intradermal flu vaccines based on inactivated virus have been studied in previous years, the fact that no intradermal flu vaccine is currently on the market reflects the difficulty to achieve effective vaccination via this route.

It has now been discovered that certain trivalent influenza vaccines make particularly good intradermal vaccines which are commercially viable. In particular, a single intradermal administration of such an influenza virus vaccine preparation stimulates systemic immunity at a protective level with a low dose of antigen. Furthermore, the international criteria for an effective flu vaccine are met. More specifically, intradermal administration of the low antigen dose vaccine can produce a systemic seroconversion (4-fold increase in anti-HA titres) equivalent to that obtained by s.c. administration of the same vaccine.

As used herein, the term "intradermal delivery" means delivery of the vaccine to the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

The invention provides in a first aspect the use of a trivalent, non-live influenza antigen preparation in the manufacture of a one-dose influenza vaccine for intradermal delivery. The influenza antigen preparation may be produced according to a variety of known methods, including in particular methods described herein. Preferably the non-live antigen preparation is a split influenza preparation or a subunit antigen preparation prepared from live virus. Most preferably the antigen is a split virus preparation.

The trivalent vaccine according to the invention meets some or all of the EU criteria for influenza vaccines as set out hereinabove, such that the vaccine is capable of being approved for marketing in Europe. Preferably, at least two out of the three EU criteria are met, for the or all strains of influenza represented in the vaccine. More preferably, at least two criteria are met for all strains and the third criterion is met by all strains or at least by all but one of the strains. Most preferably, all strains present meet all three of the criteria.

Preferably the intradermal vaccine described herein comprises at least one non-ionic surfactant which may be selected from the group consisting of the octyl- or nonylphenoxy polyoxyethanols (for example the commercially available Triton™ series), polyoxyethylene sorbitan esters (Tween™ series) and polyoxyethylene ethers or esters of general formula (I):

$$HO(CH_2CH_2O)_n\text{-}A\text{-}R \quad (I)$$

wherein n is 1-50, A is a bond or —C(O)—, R is C1-50 alkyl or phenyl C1-50 alkyl; and combinations of two or more of these.

Preferred is a combination of two non-ionic surfactants, one from each of the octylphenoxy polyoxyethanols and the polyoxyethylene sorbitan esters, in particular a combination of Tween 80 and Triton X-100. Further possible and preferred combinations of detergents are discussed hereinbelow.

The vaccine according to the invention has a lower quantity of haemagglutinin than conventional vaccines and is administered in a lower volume. Preferably the quantity of haemagglutinin per strain of influenza is about 1-7.5 µg or 1-5 µg, more preferably approximately 3 µg or approximately 5 µg, which is about one fifth or one third, respectively, of the dose of haemagglutinin used in conventional vaccines for intramuscular administration. 6 µg of haemagglutinin per strain of influenza is also strongly preferred, thus 2-6.5 µg is also a preferred range.

Preferably the volume of a dose of vaccine according to the invention is between 0.025 ml and 2.5 ml, more preferably approximately 0.1 ml or approximately 0.2 ml. A 50 µl dose volume might also be considered. A 0.1 ml dose is approximately one fifth of the volume of a conventional intramuscular flu vaccine dose. The volume of liquid that can be administered intradermally depends in part upon the site of the injection. For example, for an injection in the deltoid region, 0.1 ml is the maximum preferred volume whereas in the lumbar region a large volume e.g. about 0.2 ml can be given.

Suitable non-live flu antigen preparations for use in the invention include an influenza antigen preparation obtainable by the following process: (i) harvesting of virus-containing material from a culture; (ii) clarification of the harvested material to remove non-virus material; (iii) concentration of the harvested virus; (iv) a further step to separate whole virus from non-virus material; (v) splitting of the whole virus using a suitable splitting agent in a density gradient centrifugation step; (vi) filtration to remove undesired materials; (vii) wherein the steps are performed in that order but not necessarily consecutively.

Preferably the virus is grown on eggs, more particularly on embryonated hen eggs, in which case the harvested material is allantoic fluid.

Preferably the clarification step is performed by centrifugation at a moderate speed. Alternatively a filtration step may be used for example with a 0.2 µm membrane. The clarification step gets rid of the bulk of the egg-derived material.

Preferably the concentration step employs an adsorption method, most preferably using $CaHPO_4$. Alternatively filtration may be used, for example ultrafiltration.

Preferably the further separation step (iv) is a zonal centrifugation separation, particularly one using a sucrose gradient. Optionally the gradient contains a preservative to prevent microbial growth.

Preferably the splitting step is performed in a further sucrose gradient, wherein the sucrose gradient contains the splitting agent.

Preferably the filtration step (vi) is an ultrafiltration step which concentrates the split virus material.

Preferably there is at least one sterile filtration step, optionally at the end of the process.

Optionally there is an inactivation step prior to the final filtration step.

Preferably the vaccines according to the invention are administered to a location between about 1.0 mm and 2.0 mm below the surface of the skin. More preferably the vaccine is delivered to a distance of about 1.5 mm below the surface of the skin.

The vaccine to which the invention relates is a split virion vaccine comprising particles. Preferably the vaccine contains particles having a mean particle size below 200 nm, more preferably between 50 and 180 nm, most preferably between 100 and 150 nm, as measured using a dynamic light scattering method (Malvern Zeta Sizer). Particle size may vary from season to season depending on the strains.

Preferred surfactants falling within formula (I) herein are molecules in which n is 4-24, more preferably 6-12, and most preferably 9; the R component is $C_{1-50}$, preferably $C_4$-$C_{20}$ alkyl and most preferably $C_{12}$ alkyl.

Octylphenoxy polyoxyethanols and polyoxyethylene sorbitan esters are described in "Surfactant systems" Eds: Attwood and Florence (1983, Chapman and Hall). Octylphenoxy polyoxyethanols (the octoxynols), including t-octylphenoxypolyethoxyethanol (Triton X-100™) are also described in Merck Index Entry 6858 (Page 1162, 12th Edition, Merck & Co. Inc., Whitehouse Station, N.J., USA; ISBN 0911910-12-3). The polyoxyethylene sorbitan esters, including polyoxyethylene sorbitan monooleate (Tween 80™) are described in Merck Index Entry 7742 (Page 1308, 12th Edition, Merck & Co. Inc., Whitehouse Station, N.J., USA; ISBN 0911910-12-3). Both may be manufactured using methods described therein, or purchased from commercial sources such as Sigma Inc.

Particularly preferred non-ionic surfactants include Triton X-45, t-octylphenoxy polyethoxyethanol (Triton X-100), Triton X-102, Triton X-114, Triton X-165, Triton X-205, Triton X-305, Triton N-57, Triton N-101, Triton N-128, Breij 35, polyoxyethylene-9-lauryl ether (laureth 9) and polyoxyethylene-9-stearyl ether (steareth 9). Triton X-100 and laureth 9 are particularly preferred. Also particularly preferred is the polyoxyethylene sorbitan ester, polyoxyethylene sorbitan monooleate (Tween 80™).

Further suitable polyoxyethylene ethers of general formula (I) are selected from the following group: polyoxyethylene-8-stearyl ether, polyoxyethylene-4-lauryl ether, polyoxyethylene-35-lauryl ether, and polyoxyethylene-23-lauryl ether.

Alternative terms or names for polyoxyethylene lauryl ether are disclosed in the CAS registry. The CAS registry number of polyoxyethylene-9 lauryl ether is: 9002-92-0. Polyoxyethylene ethers such as polyoxyethylene lauryl ether are described in the Merck index (12th ed: entry 7717, Merck & Co. Inc., Whitehouse Station, N.J., USA; ISBN 0911910-12-3). Laureth 9 is formed by reacting ethylene oxide with dodecyl alcohol, and has an average of nine ethylene oxide units.

The ratio of the length of the polyoxyethylene section to the length of the alkyl chain in the surfactant (i.e. the ratio of n: alkyl chain length), affects the solubility of this class of surfactant in an aqueous medium. Thus, the surfactants of the present invention may be in solution or may form particulate structures such as micelles or vesicles. As a solution, the surfactants of the present invention are safe, easily sterilisable, simple to administer, and may be manufactured in a simple fashion without the GMP and QC issues associated with the formation of uniform particulate structures. Some polyoxyethylene ethers, such as laureth 9, are capable of forming non-vesicular solutions. However, polyoxyethylene-8 palmitoyl ether (C18E8) is capable of forming vesicles. Accordingly, vesicles of polyoxyethylene-8 palmitoyl ether in combination with at least one additional non-ionic surfactant, can be employed in the formulations of the present invention.

Preferably, the polyoxyethylene ether used in the formulations of the present invention has haemolytic activity. The haemolytic activity of a polyoxyethylene ether may be measured in vitro, with reference to the following assay, and is as expressed as the highest concentration of the surfactant which fails to cause lysis of the red blood cells:

1. Fresh blood from guinea pigs is washed with phosphate buffered saline (PBS) 3 times in a desk-top centrifuge. After re-suspension to the original volume the blood is further diluted 10 fold in PBS.
2. 50 µl of this blood suspension is added to 800 µl of PBS containing two-fold dilutions of detergent.
3. After 8 hours the haemolysis is assessed visually or by measuring the optical density of the supernatant. The presence of a red supernatant, which absorbs light at 570 nm indicates the presence of haemolysis.
4. The results are expressed as the concentration of the first detergent dilution at which hemolysis no longer occurs.

Within the inherent experimental variability of such a biological assay, the polyoxyethylene ethers, or surfactants of general formula (I), of the present invention preferably have a haemolytic activity, of approximately between 0.5-0.0001%, more preferably between 0.05-0.0001%, even more preferably between 0.005-0.0001%, and most preferably between 0.003-0.0004%. Ideally, said polyoxyethylene ethers or esters should have a haemolytic activity similar (i.e. within a ten-fold difference) to that of either polyoxyethylene-9 lauryl ether or polyoxyethylene-8 stearyl ether.

Two or more non-ionic surfactants from the different groups of surfactants described may be present in the vaccine formulation described herein. In particular, a combination of a polyoxyethylene sorbitan ester such as polyoxyethylene sorbitan monooleate (Tween 80™) and an octoxynol such as t-octylphenoxypolyethoxyethanol (Triton) X-100™ is preferred. Another particularly preferred combination of non-ionic surfactants comprises laureth 9 plus a polyoxyethylene sorbitan ester or an octoxynol or both.

Preferably the or each non-ionic surfactant is present in the final vaccine formulation at a concentration of between 0.001 to 20%, more preferably 0.01 to 10%, and most preferably up to about 2% (w/v). Where one or two surfactants are present, these are generally present in the final formulation at a concentration of up to about 2% each, typically at a concentration of up to about 0.6% each. One or more additional surfactants may be present, generally up to a concentration of about 1% each and typically in traces up to about 0.2% or 0.1% each. Any mixture of surfactants may be present in the vaccine formulations according to the invention.

Non-ionic surfactants such as those discussed above have preferred concentrations in the final vaccine composition as follows: polyoxyethylene sorbitan esters such as Tween 80™: 0.01 to 1%, most preferably about 0.1% (w/v); octyl- or nonylphenoxy polyoxyethanols such as Triton X-100™ or other detergents in the Triton series: 0.001 to 0.1%, most preferably 0.005 to 0.02% (w/v); polyoxyethylene ethers of general formula (I) such as laureth 9: 0.1 to 20%, preferably 0.1 to 10% and most preferably 0.1 to 1% or about 0.5% (w/v).

Other reagents may also be present in the formulation. As such the formulations of the present invention may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particularly preferred example is sodium deoxycholate (Na-DOC) which may be present in the final vaccine dose.

The vaccine formulation according to the invention preferably comprises a split flu virus preparation in combination with one or more non-ionic surfactants. The one or more non-ionic surfactants may be residual from the process by which the split flu antigen preparation is produced, and/or added to the antigen preparation later. The concentration of the or each non-ionic surfactant may be adjusted to the desired level at the end of the splitting/purification process. It is believed that the split flu antigen material may be stabilised in the presence of a non-ionic surfactant, though it will be understood that the invention does not depend upon this necessarily being the case.

The vaccine according to the invention may further comprise an adjuvant or immunostimulant such as but not limited to detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

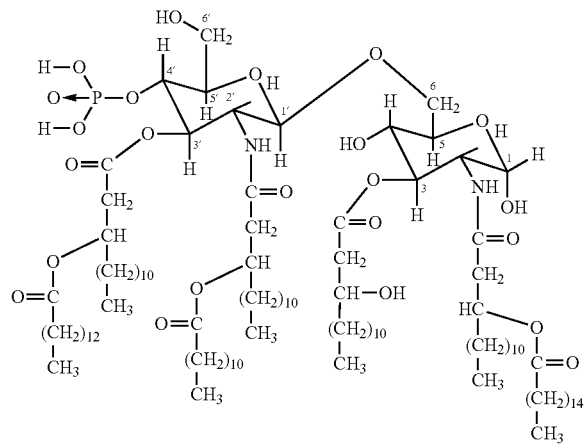

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A preferred form of 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, Int. Arch. Allergy. Immunol., 79(4):392-6; Hilgers et al., 1987, Immunology, 60(1):141-6; and EP 0 549 074 B1). A particularly preferred bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria Molina*), and fractions thereof, are described in U.S. Pat. No. 5,057,540 and "Saponins as vaccine adjuvants", Kensil, C. R., Crit. Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as *Gypsophila* and *Saponaria* (Bomford et al., Vaccine, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21 and 3D-MPL in an oil in water emulsion is described in WO 95/17210 and is a preferred formulation.

Accordingly in one embodiment of the present invention there is provided a vaccine comprising an influenza antigen preparation of the present invention adjuvanted with detoxified lipid A or a non-toxic derivative of lipid A, more preferably adjuvanted with a monophosphoryl lipid A or derivative thereof.

Preferably the vaccine additionally comprises a saponin, more preferably QS21.

Preferably the formulation additionally comprises an oil in water emulsion. The present invention also provides a method for producing a vaccine formulation comprising mixing an antigen preparation of the present invention together with a pharmaceutically acceptable excipient, such as 3D-MPL.

Additional components that are preferably present in an adjuvanted vaccine formulation according to the invention include non-ionic detergents such as the octoxynols and polyoxyethylene esters as described herein, particularly t-octylphenoxy polyethoxyethanol (Triton X-100) and polyoxyethylene sorbitan monooleate (Tween 80); and bile salts or cholic acid derivatives as described herein, in particular sodium deoxycholate or taurodeoxycholate. Thus, a particularly preferred formulation comprises 3D-MPL, Triton X-100, Tween 80 and sodium deoxycholate, which may be combined with an influenza virus antigen preparation to provide a vaccine suitable for intradermal application.

In one preferred embodiment of the present invention, the intradermal influenza vaccines comprise a vesicular adjuvant formulation comprising. In this regard the preferred adjuvant formulation comprises a unilamellar vesicle comprising cholesterol, having a lipid bilayer preferably comprising dioleoyl phosphatidyl choline, wherein the saponin and the LPS derivative are associated with, or embedded within, the lipid bilayer. More preferably, these adjuvant formulations comprise QS21 as the saponin, and 3D-MPL as the LPS derivative, wherein the ratio of QS21:cholesterol is from 1:1 to 1:100 weight/weight, and most preferably 1:5 weight/weight. Such adjuvant formulations are described in EP 0 822 831 B, the disclosure of which is incorporated herein by reference.

The invention also provides a method for the prophylaxis of influenza infection or disease in a subject which method comprises administering to the subject intradermally a split influenza vaccine according to the invention.

The invention provides in a further aspect a pharmaceutical kit comprising an intradermal administration device and a vaccine formulation as described herein. The device is preferably supplied already filled with the vaccine. Preferably the vaccine is in a liquid volume smaller than for conventional intramuscular vaccines as described herein, particularly a volume of between about 0.05 ml and 0.2 ml. Preferably the device is a short needle delivery device for administering the vaccine to the dermis.

Suitable devices for use with the intradermal vaccines described herein include short needle devices such as those described in U.S. Pat. No. 4,886,499, U.S. Pat. No. 5,190,521, U.S. Pat. No. 5,328,483, U.S. Pat. No. 5,527,288, U.S. Pat. No. 4,270,537, U.S. Pat. No. 5,015,235, U.S. Pat. No. 5,141,496, U.S. Pat. No. 5,417,662. Intradermal vaccines may also be administered by devices which limit the effective penetration length of a needle into the skin, such as those described in WO99/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration. However, the use of conventional syringes requires highly skilled operators and thus devices which are capable of accurate delivery without a highly skilled user are preferred.

The influenza vaccine according to the invention is a trivalent influenza vaccine generally comprising three strains of influenza, although it may contain more than three strains. Conventional influenza vaccines comprise three strains of influenza, two A strains and one B strain.

The influenza virus preparations may be derived from the conventional embryonated egg method, or they may be derived from any of the new generation methods using tissue culture to grow the virus. Suitable cell substrates for growing the virus include for example dog kidney cells such as MDCK or cells from a clone of MDCK, MDCK-like cells, monkey kidney cells such as AGMK cells including Vero cells, or any other mammalian cell type suitable for the production of influenza virus for vaccine purposes. Suitable cell substrates also include human cells e.g. MRC-5 cells. Suitable cell substrates are not limited to cell lines; for example primary cells such as chicken embryo fibroblasts are also included.

Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including Triton X-100 (for example in a process described in Lina et al, 2000, Biologicals 28, 95-103) and Triton N-101, or combinations of any two or more detergents.

Further suitable splitting agents which can be used to produce split flu virus preparations include:

1. Bile acids and derivatives thereof including: cholic acid, deoxycholic acid, chenodeoxy colic acid, lithocholic acid ursodeoxycholic acid, hyodeoxycholic acid and derivatives like glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particular example is sodium deoxycholate (NaDOC) which may be present in trace amounts in the final vaccine dose.
2. Alkylglycosides or alkylthioglycosides, where the alkyl chain is between C6-C18 typical between C8 and C14, sugar moiety is any pentose or hexose or combinations thereof with different linkages, like 1->6, 1->5, 1->4, 1->3, 1-2. The alkyl chain can be saturated unsaturated and/or branched.
3. Derivatives of 2 above, where one or more hydroxyl groups, preferably the 6 hydroxyl group is/are modified, like esters, ethoxylates, sulphates, ethers, carbonates, sulphosuccinates, isethionates, ethercarboxylates, quarternary ammonium compounds.
4. Acyl sugars, where the acyl chain is between C6 and C18, typical between C8 and C12, sugar moiety is any pentose or hexose or combinations thereof with different linkages, like 1->6, 1->5, 1->4, 1->3, 1-2. The acyl chain can be saturated or unsaturated and/or branched, cyclic or non-cyclic, with or without one or more heteroatoms e.g. N, S, P or O.
5. Sulphobetaines of the structure R—N,N—(R1,R2)-3-amino-1-propanesulfonate, where R is any alkyl chain or arylalkyl chain between C6 and C18, typical between C8 and C16. The alkyl chain R can be saturated, unsaturated and/or branched. R1 and R2 are preferably alkyl chains between C1 and C4, typically C1, or R1, R2 can form a heterocyclic ring together with the nitrogen.

6. Betains of the structure R—N,N—(R1,R2)-glycine, where R is any alkyl chain between C6 and C18, typical between C8 and C16. The alkyl chain can be saturated unsaturated and/or branched. R1 and R2 are preferably alkyl chains between C1 and C4, typically C1, or R1 and R2 can form a heterocyclic ring together with the nitrogen.
7. N,N-dialkyl-glucamides, of the Structure R—(N—R1)-glucamide, where R is any alkylchain between C6 and C18, typical between C8 and C12. The alkyl chain can be saturated unsaturated and/or branched or cyclic. R1 and R2 are alkyl chains between C1 and C6, typically C1. The sugar moiety might be modified with pentoses or hexoses.
8. Quarternary ammonium compounds of the structure R, —$N^+$ (—R1, —R2, —R3), where R is any alkylchain between C6 and C20, typically C20. The alkyl chain can be saturated unsaturated and/or branched. R1, R2 and R3 are preferably alkyl chains between C1 and C4, typically C1, or R1, R2 can form a heterocyclic ring together with the nitrogen. A particular example is cetyl trimethyl ammonium bromide (CTAB).

The preparation process for a split vaccine will include a number of different filtration and/or other separation steps such as ultracentrifugation, ultrafiltration, zonal centrifugation and chromatography (e.g. ion exchange) steps in a variety of combinations, and optionally an inactivation step e.g. with formaldehyde or β-propiolactone or U.V. which may be carried out before or after splitting. The splitting process may be carried out as a batch, continuous or semi-continuous process.

Preferably, a bile salt such as sodium deoxycholate is present in trace amounts in a split vaccine formulation according to the invention, preferably at a concentration not greater than 0.05%, or not greater than about 0.01%, more preferably at about 0.0045% (w/v).

Preferred split flu vaccine antigen preparations according to the invention comprise a residual amount of Tween 80 and/or Triton X-100 remaining from the production process, although these may be added or their concentrations adjusted after preparation of the split antigen. Preferably both Tween 80 and Triton X-100 are present. The preferred ranges for the final concentrations of these non-ionic surfactants in the vaccine dose are: Tween 80: 0.01 to 1%, more preferably about 0.1% (v/v); Triton X-100: 0.001 to 0.1 (% w/v), more preferably 0.005 to 0.02% (w/v).

The presence of the combination of these two surfactants, in low concentrations, was found to promote the stability of the antigen in solution. It is possible that this enhanced stability rendered the antigen more immunogenic intradermally than previous formulations have been. Such an enhancement could arise from a prevalence of small antigen aggregates or the enhancement of the native conformation of the antigen. It will be appreciated that the invention does not depend upon this theoretical explanation being correct.

In a particular embodiment, the preferred split virus preparation also contains laureth 9, preferably in the range 0.1 to 20%, more preferably 0.1 to 10% and most preferably 0.1 to 1% (w/v).

The vaccines according to the invention generally contain not more than 25% (w/v) of detergent or surfactant, preferably less than 15% and most preferably not more than about 2%.

The invention provides in another aspect a method of manufacturing an influenza vaccine for intradermal application which method comprises:

(i) providing a split influenza virus preparation produced essentially as for a conventional injected (e.g. intramuscular) influenza vaccine and comprising at least one non-ionic surfactant;

(ii) optionally adjusting the concentration of the haemagglutinin and/or the concentration of non-ionic surfactant in the preparation;

(iii) filling an intradermal delivery device with a vaccine dose from the split influenza virus preparation, said dose being a suitable volume for intradermal administration, preferably between about 0.05 ml and 0.2 ml of liquid vaccine.

A further optional step in the method according to this aspect of the invention includes the addition of an absorption-enhancing surfactant such as laureth 9, and/or the addition of an adjuvant such as a non-toxic lipid A derivative, particularly 3D-MPL.

Processes for producing conventional injected inactivated flu vaccines are well known and described in the literature. Such processes may be modified for producing a one-dose intradermal vaccine for use in the present invention, for example by the inclusion of a step for adjusting the concentration of other components e.g. non-ionic surfactants to a suitable % (w/v) for an intradermal vaccine according to the invention. However, the active ingredient of the vaccine, i.e. the influenza antigen can be essentially the same for the conventional intramuscular vaccine and the one-dose intradermal vaccines according to the invention.

Preferably, the vaccine formulations according to the invention do not include formulations that do not meet at least two of the EU criteria for all strains, when administered as a one-dose vaccine.

The invention will now be further described in the following, non-limiting examples.

EXAMPLES

Example 1

Preparation of Split Influenza Vaccine

Each strain for the split vaccine was prepared according to the following procedure.
Preparation of Virus Inoculum On the day of inoculation of embryonated eggs a fresh inoculum was prepared by mixing the working seed lot with a phosphate buffered saline containing gentamycin sulphate at 0.5 mg/ml and hydrocortisone at 25 μg/ml. (virus strain-dependent). The virus inoculum was kept at 2-8° C.
Inoculation of Embryonated Eggs Nine to eleven day old embryonated eggs were used for virus replication. Shells were decontaminated. The eggs were inoculated with 0.2 ml of the virus inoculum. The inoculated eggs were incubated at the appropriate temperature (virus strain-dependent) for 48 to 96 hours. At the end of the incubation period, the embryos were killed by cooling and the eggs were stored for 12-60 hours at 2-8° C.
Harvest The allantoic fluid from the chilled embryonated eggs was harvested. Usually, 8 to 10 ml of crude allantoic fluid was collected per egg. To the crude monovalent virus bulk 0.100 mg/ml thiomersal was optionally added.
Concentration and Purification of Whole Virus from Allantoic Fluid
1. Clarification The harvested allantoic fluid was clarified by moderate speed centrifugation (range: 4000-14000 g).

2. Adsorption Step

To obtain a CaHPO$_4$ gel in the clarified virus pool, 0.5 mol/L Na$_2$HPO$_4$ and 0.5 mol/L CaCl$_2$ solutions were added to reach a final concentration of CaHPO$_4$ of 1.5 g to 3.5 g CaHPO$_4$/liter depending on the virus strain.

After sedimentation for at last 8 hours, the supernatant was removed and the sediment containing the influenza virus is resolubilised by addition of a 0.26 mol/L EDTA-Na$_2$ solution, dependent on the amount of CaHPO$_4$ used.

3. Filtration

The resuspended sediment was filtered on a 6 μm filter membrane.

4. Sucrose Gradient Centrifugation

The influenza virus was concentrated by isopycnic centrifugation in a linear sucrose gradient (0-55% (w/v)) containing 100 μg/ml Thiomersal. The flow rate was 8-15 liters/hour.

At the end of the centrifugation, the content of the rotor was recovered by four different fractions (the sucrose is measured in a refractometer):

fraction 1 55-52% sucrose
fraction 2 approximately 52-38% sucrose
fraction 3 38-20% sucrose*
fraction 4 20-0% sucrose

* virus strain-dependent: fraction 3 can be reduced to 15% sucrose.

For further vaccine preparation, only fractions 2 and 3 were used.

Fraction 3 was washed by diafiltration with phosphate buffer in order to reduce the sucrose content to approximately below 6%. The influenza virus present in this diluted fraction was pelleted to remove soluble contaminants.

The pellet was resuspended and thoroughly mixed to obtain a homogeneous suspension. Fraction 2 and the resuspended pellet of fraction 3 were pooled and phosphate buffer was added to obtain a volume of approximately 40 liters. This product was the monovalent whole virus concentrate.

5. Sucrose Gradient Centrifugation with Sodium Deoxycholate

The monovalent whole influenza virus concentrate was applied to a ENI-Mark II ultracentrifuge. The K3 rotor contained a linear sucrose gradient (0-55% (w/v)) where a sodium deoxycholate gradient was additionally overlayed. Tween 80 was present during splitting up to 0.1% (w/v). The maximal sodium deoxycholate concentration was 0.7-1.5% (w/v) and was strain dependent. The flow rate was 8-15 liters/hour.

At the end of the centrifugation, the content of the rotor was recovered by three different fractions (the sucrose is measured in a refractometer). Fraction 2 was used for further processing. Sucrose content for fraction limits (47-18%) varied according to strains and is fixed after evaluation.

6. Sterile Filtration

The split virus fraction was filtered on filter membranes ending with a 0.2 μM membrane. Phosphate buffer containing 0.025% (w/v) Tween 80 was used for dilution. The final volume of the filtered fraction 2 was 5 times the original fraction volume.

7. Inactivation

The filtered monovalent material was incubated at 22±2° C. for at most 84 hours (dependent on the virus strains, this incubation can be shortened). Phosphate buffer containing 0.025% Tween 80 was then added in order to reduce the total protein content down to max. 250 μg/ml. Formaldehyde was added to a final concentration of 50 μg/ml and the inactivation took place at 20° C.±2° C. for at least 72 hours.

8. Ultrafiltration

The inactivated split virus material was concentrated at least 2 fold in a ultrafiltration unit, equipped with cellulose acetate membranes with 20 kDa MWCO. The material was subsequently washed with phosphate buffer containing 0.025% (w/v) Tween 80 and following with phosphate buffered saline containing 0.01% (w/v) Tween.

9. Final Sterile Filtration

The material after ultrafiltration was filtered on filter membranes ending with a 0.2 μm membrane. The final concentration of Haemagglutinin, measured by SRD (method recommended by WHO) should exceed 450 μg/ml.

10. Storage

The monovalent final bulk was stored at 2-8° C. for a maximum of 18 months.

Purity

Purity was determined semiquantitatively by O.D. scanning of Coomassie-stained polyacrylamide gels. Peaks were determined manually. Sample results are given in Table 1:

TABLE 1

| | Viral Proteins (HA, NP, M) % | | | | Other viral and host-cell derived |
|---|---|---|---|---|---|
| H3N2 | HA dimer | HA1 + 2 | NP | M | proteins % |
| A/Syd/5/97 | 10.34 | 22.34 | 25.16 | 37.33 | 4.83 |
| A/Nan933/95 | 8.17 | 15.8 | 40.09 | 30.62 | 5.32 |
| B | | | | | |
| B/Har/7/94 | 5.71[2] | 24.07 | 15.64 | 50 | 4.58 |
| B/Yam/166/98 | 0.68 | 27.62 | 21.48 | 46.02 | 4.2 |
| H1N1 | | | | | |
| A/Tex/36/91 | | 33.42 | 24.46 | 34.33 | 7.79 |
| A/Bei/262/95 | | 32.73 | 35.72 | 27.06 | 4.49 |
| H2N2 | | | | | |
| A/sing/1/57 | 2.8 | 39.7 | 21.78 | 32.12 | 3.6 |

A particular combination of strains includes A/New Caledonia/20/99 (H1N1), A/Panama/20/99 (H3N2) and B/Yamanashi/166/98.

Example 2

Preparation of Vaccine Doses from Bulk Vaccine

Final vaccine was prepared by formulating a trivalent vaccine from the monovalent bulks with the detergent concentrations adjusted as required.

PBS, pH 7.2+/−0.2, Tween 80 and Triton X-100 are mixed to obtain the required final concentrations (PBS 1× concentrated, Tween 80 0.15% and Triton X-100 0.02%). The three following inactivated split virions are added with 10 minutes stirring in between:

15 μg A/New Caledonia/20/99 (H1N1)

15 μg A/Panama/20/99 (H3N2)

15 μg B/Yamanashi/166/98

After 15 minutes stirring pH is adjusted to 7.2+/−0.2. The dose volume is 500 μl. The doses are filled in sterile ampoules. Immediately before applying the vaccine, 0.1 ml doses are removed from the ampoule using the device for intradermal application.

Example 3

Methods Used to Measure Antibody Responses

1. Detection of Specific Anti-Flu and Total IgA in Human Nasal Secretions by ELISA Collection Method for Human Nasal Secretions An appropriate method was used to collect nasal secretions, for example a classical nasal wash method or a nasal wick method.

After collection and treatment of human nasal secretions, the detection of total and specific anti-FLU IgA was realized with ELISAs e.g.:

Capture ELISA for Detection of Total IgA

Total IgA were captured with anti-human IgA polyclonal affinity purified Ig immobilized on microtiter plates and subsequently detected using a different polyclonal anti-human IgA affinity purified Ig coupled to peroxidase. A purified human sIgA was used as a standard to allow the quantification of sIgA in the collected nasal secretions. The 3 references of purified human sIgA were used as low, medium and high references in this assay.

Direct ELISA for Detection of Specific Anti-FLU IgA

Three different ELISAs were performed, one on each FLU strain present in the vaccine formulation. Specific anti-FLU IgA were captured with split inactivated FLU antigens coated on microtiter plates and subsequently detected using the same different polyclonal anti-human IgA affinity purified Ig coupled to peroxidase as the one used for the total IgA ELISA.

Results—Expression and Calculations

Total IgA Expression

The results were expressed as µg of total IgA in 1 ml of nasal fluids, using a Softmaxpro program.

Specific Anti-Flu IgA Expression

The results were expressed as end-point unit titer, which are calculated as the inverse of the last dilution which gives an OD450 nm above the cut off.

The final results of a sample were expressed as follows:

Normalization of the specific response by calculating the ratio between the specific response and the total IgA concentration: end-point unit/µg total IgA (most commonly used calculation method in the literature).

2. Haemagglutination Inhibition (HAI) Activity of Flu-Specific Serum Abs

Sera (50 µl) are treated with 200 µl RDE (receptor destroying enzyme) for 16 hours at 37° C. The reaction is stopped with 150 µl 2.5% Na citrate and the sera are inactivated at 56° C. for 30 min. A dilution 1:10 is prepared by adding 100 µl PBS. Then, a 2-fold dilution series is prepared in 96 well plates (V-bottom) by diluting 25 µl serum (1:10) with 25 µl PBS. 25 µl of the reference antigens are added to each well at a concentration of 4 hemagglutinating units per 25 µl. Antigen and antiserum dilution are mixed using a microtiter plate shaker and incubated for 60 minutes at room temperature. 50 µl chicken red blood cells (RBC) (0.5%) are then added and the RBCs are allowed to sediment for 1 hour at RT. The HAI titre corresponds to the inverse of the last serum dilution that completely inhibits the virus-induced hemagglutination.

Example 4

Immunogenicity and Reactogenicity of Flu ID

Clinical trials were carried out on human subjects to assess efficacy of the influenza vaccine of the invention delivered ID. The vaccine (Fluarix™) used in this study was made according to Examples 1 and 2.

A hundred healthy male and female volunteers (18-60 years of age) were enrolled and randomised in 2 groups (50 subjects per group). The vaccine was administered according two routes of administration.

Intramuscularly administered trivalent split influenza vaccine (Fluarix™):

1 dose→Day 0.

The vaccine was supplied as a pre-filled syringe for intramuscular injection in the deltoid region of the non-predominant arm. In order to ensure proper intramuscular injection of the study vaccines, a needle of at least 23G (2.2 cm/1 in.) length was used.

Intradermally administered trivalent split influenza vaccine (Fluarix™):

⅕ dose→Day 0

The vaccine was supplied as 0.5 ml ampoule dose. ⅕ of the full dose (1000) was injected intradermally using a device as disclosed in EP1092444, the whole contents of which are herein incorporated by reference. The device has a skin contacting element that effectively limits the penetration depth of the needle into the dermis. Effective needle length was approximately 1.5 mm. This device is herein referred to as the ID delivery device or 'IDD'.

The duration of the study was approximately 21 days per subject with only one dose of the vaccine given intramuscularly or intradermally according to the group. Blood was sampled at day 0 and 21.

The Study Population were as Follows:

| Group 1 | Group 2 |
|---|---|
| Fluarix ™ Intramuscular | Fluarix ™ Intradermal with IDD |
| 0.5 ml of Fluarix ™, lot n° 18500A9 | 0.1 ml of Fluarix ™, lot n° 018526B7 |
| N = 50 | N = 50 |

The demographic profile of the 2 groups of subjects who received vaccine was comparable with respect to mean age, gender and racial distribution.

Immunogenicity

For each treatment group, the following parameters for immunogenicity were calculated:

Geometric mean titres (GMTs) (with 95% confidence intervals) of HI antibody titres at days 0 and 21, calculated by taking the anti-log of the mean of the log titre transformations (titres below the cut-off value were given the arbitrary value of half the cut-off for calculation purpose).

Seropositivity (S+) rates of HI antibody titres at days 0 and 21, defined as the percentage of subjects with titre greater than or equal to the assay cut-off.

Conversion factors at day 21 defined as the fold increase in serum HI GMTs on day 21 compared to day 0.

Seroconversion rates (SC) at day 21 defined as the percentage of vaccinees who have at least a 4-fold increase in serum HI titres on day 21 compared to day 0.

Protection rates at day 21 defined as the percentage of vaccinees with a serum HI titre≥1:40 after vaccination.

Laboratory Assays and Timepoints

All serum samples were kept at −20° C. and adequate measures taken to insure that samples did not thaw at any time. At each visit, blood was collected for measurement of HI antibody response.

The immune response was determined by the titre of haemagglutination-inhibiting antibodies (HAI) measured by the haemagglutination-inhibition test described by the WHO Collaborating Centre for Influenza, Centres for Diseases Control, Atlanta, USA (1991).

Frozen serum samples were received at Sächsisches Serumwerk GmbH (SSW), Dresden, Germany and antibody determination was conducted on samples after thawing, with a standardised and comprehensively validated micromethod using 4 haemagglutination-inhibiting units (4 HIU) of the appropriate antigens and a 0.5% fowl erythrocyte suspension. The antigens A (H3N2 and H1N1) were obtained as whole virus antigens from the allantoic fluid of embryonated hens' eggs. The B antigen was subjected to cleavage with a mixture of ether and Tween 80 to increase sensitivity. Non-specific serum inhibitors were removed by heat treatment and receptor-destroying enzyme.

The sera obtained were evaluated for HI antibody levels. Starting with an initial dilution of 1:10, a dilution series (by a factor of 2) is prepared up to an end dilution of 1:20480. The titration end-point is taken as the highest dilution step that shows complete inhibition (100%) of haemagglutination. All assays were performed in duplicate.

Results

The number of subjects being the same in the ATP immunogenicity cohort and the total cohort, the immunogenicity analysis was performed only on an intent-to-treat (ITT) basis (i.e. total cohort).

HI Titres and Conversion Factors

The Geometric mean titres (GMTs) (with 95% confidence intervals) of HI antibody titres at days 0 and 21, for the three groups are given in the table below:

| Seropositivity rates and Geometric Mean Titres (GMT) (Total cohort) | | | | | | | |
|---|---|---|---|---|---|---|---|
| Antibody | Group | Timing | GMT | L.L. | U.L. | MIN | MAX |
| A/NEW-CALEDONIA | Fluarix ™ IM | PRE | 66.3 | 45.8 | 96.0 | <10.0 | 905.0 |
|  |  | PI(D21) | 725.0 | 536.2 | 980.2 | 80.0 | 5120.0 |
|  | Fluarix ™ ID with IDD | PRE | 34.3 | 24.1 | 48.8 | <10.0 | 640.0 |
|  |  | PI(D21) | 313.3 | 223.1 | 440.1 | 28.0 | 2560.0 |
| A/PANAMA | Fluarix ™ IM | PRE | 40.6 | 28.2 | 58.3 | <10.0 | 640.0 |
|  |  | PI(D21) | 365.1 | 262.8 | 507.1 | 40.0 | 5120.0 |
|  | Fluarix ™ ID with IDD | PRE | 23.9 | 17.1 | 33.6 | <10.0 | 453.0 |
|  |  | PI(D21) | 220.2 | 149.0 | 325.3 | 10.0 | 5120.0 |
| B/YAMANASHI | Fluarix ™ IM | PRE | 90.0 | 65.4 | 123.7 | <10.0 | 640.0 |
|  |  | PI(D21) | 983.6 | 741.0 | 1305.6 | 160.0 | 7241.0 |
|  | Fluarix ™ using ID delivery device | PRE | 49.5 | 33.0 | 74.4 | <10.0 | 1280.0 |
|  |  | PI(D21) | 422.2 | 316.2 | 563.8 | 20.0 | 2560.0 |

PRE = pre-vaccination;
PI (D21) = day 21 post vaccination
95% CI, L.L., and U.L. = 95% confidence intervals, lower and upper limit
The total number of subjects was 50 in each group The differences for the three strains (New Caledonia, A/Panama, and B/Yamanashi), between the groups on day 0 were non-significant (p>0.05). On day 21, significant (p<0.0001) differences were observed between the ID group and the IM group. However, when the increases in titres from day 0 to day 21 (conversion factor, see Table below) were compared, no significant difference was measured (p>0.05) from one group to the other, meaning that the increases were globally comparable.

HI results do not allow discrimination between the intradermal vaccine group and the Fluarix™ intramuscular vaccine group.

| Conversion factor (Total cohort). | | | | |
|---|---|---|---|---|
| Group | N | A/N-Caledonia [95% CI] | A/Panama [95% CI] | B/Yamanashi [95% CI] |
| Fluarix IM. | 50 | 10.6 [7.2-15.6] | 9.3 [6.0-14.2] | 10.9 [7.6-15.7] |
| Fluarix using ID delivery device | 50 | 9.1 [6.2-13.3] | 9.2 [5.6-15.2] | 8.5 [5.7-12.8] |

The conversion factor (fold increase in serum HI GMTs on day 21 compared to day 0) varies from 8.5 to 10.9 according the virus strains and the route of administration (see Table above). This conversion factor is superior to the 2.5 fold increase in GMT required by the European Authorities.

An analysis of variance with the factor treatment as classification criterion was used to compare the conversion factors. No significant difference was measured between the treatment groups (p>0.05).

Seroprotection Rate

The seroprotection rate shown in the Table below is defined as the percentage of vaccinees with a serum HI titre≥40 after vaccination.

| Distribution of individual antibody titres and protection rates (Total cohort) | | | | | | | |
|---|---|---|---|---|---|---|---|
|  |  |  |  | <40 | | >=40 | |
| Antibody | Group | Timing | N | n | % | n | % |
| A/NEW-CALEDONIA | Fluarix ™ IM | PRE | 50 | 15 | 30.0 | 35 | 70.0 |
|  |  | PI(D21) | 50 | 0 | 0.0 | 50 | 100.0 |
|  | Fluarix ™ ID with IDD | PRE | 50 | 26 | 52.0 | 24 | 48.0 |
|  |  | PI(D21) | 50 | 1 | 2.0 | 49 | 98.0 |
| A/PANAMA | Fluarix ™ IM | PRE | 50 | 21 | 42.0 | 29 | 58.0 |
|  |  | PI(D21) | 50 | 0 | 0.0 | 50 | 100.0 |
|  | Fluarix ™ ID with IDD | PRE | 50 | 29 | 58.0 | 21 | 42.0 |
|  |  | PI(D21) | 50 | 2 | 4.0 | 48 | 96.0 |

-continued

Distribution of individual antibody titres and protection rates (Total cohort)

| Antibody | Group | Timing | N | <40 n | <40 % | >=40 n | >=40 % |
|---|---|---|---|---|---|---|---|
| B/YAMANASHI | Fluarix ™ IM | PRE | 50 | 8 | 16.0 | 42 | 84.0 |
| | | PI(D21) | 50 | 0 | 0.0 | 50 | 100.0 |
| | Fluarix ™ ID with IDD | PRE | 50 | 20 | 40.0 | 30 | 60.0 |
| | | PI(D21) | 50 | 1 | 2.0 | 49 | 98.0 |

PRE = pre-vaccination,
PI (D21) = day 21 post vaccination
N = number of subjects tested.
n = number of subjects with HI titres < or >=40
% = n/N × 100%
<40: Titres less than 40 HIU
>=40: Titres more than or equal to 40 HIU At day 21, the seroprotection rates in the groups ranged from 96% to 100% for the different virus strains. In terms of protection, this means that more than 95% of the subjects (whatever the route of administration) had a serum HI titre≥40 after vaccination and were deemed to be protected against the three strains. This rate is superior to the seroprotection rate of 70% required in the 18-60 year old population, by the European Authorities.

Seroconversion Rate.

The seroconversion factor given in the Table below is defined as the percentage of vaccinees that have at least a 4-fold increase in serum HI titres after vaccination.

Vaccine responses and seroconversion (Total cohort)

| Antibody | Group | Prevacc. Status | N | Responders n | Responders % | 95% CI LL | 95% CI UL |
|---|---|---|---|---|---|---|---|
| A/NEW-CALEDONIA | Fluarix ™ IM | Total | 50 | 39 | 78 | 64 | 88.5 |
| | Fluarix ™ ID with IDD | Total | 50 | 37 | 74 | 59.7 | 85.4 |
| A/PANAMA | Fluarix ™ IM | Total | 50 | 36 | 72 | 57.5 | 83.8 |
| | Fluarix ™ with IDD | Total | 50 | 33 | 66 | 51.2 | 78.8 |
| B/YAMANASHI | Fluarix ™ IM | Total | 50 | 40 | 80 | 66.3 | 90 |
| | Fluarix ™ ID with IDD | Total | 50 | 35 | 70 | 55.4 | 82.1 |

95% CI, L.L., and U.L. = 95% confidence intervals, lower and upper limit
N = number of subject tested
n = number of subject responding to vaccination.
% = n/N × 100%

To be deemed effective and according to European Authority requirements, a vaccine should induce a seroconversion rate greater than 40% in the 18-60 year old population. In this study, the seroconversion rate was greater than 65% for the groups.

Reactogenicity

The intradermal administration of vaccine was safe (no serious adverse events were reported) and clinically well tolerated with very few reports of general symptoms related to vaccination.

Conclusions

Fluarix™ induced good immune responses for each strain with a high seroconversion rate after one dose whatever the route of administration (ID or IM).

There was no significant difference between the immune response elicited by ⅕ dose of Fluarix™ given intradermally and by the full dose administered by the IM route.

Both vaccinations fulfilled the requirement of the European authorities for influenza inactivated vaccines in the 18-60 year old population, i.e., Induce a seroconversion rate greater than 40%.
Increase the geometric mean titre by more than 2.5.
Elicit a seroprotection rate of 70%.

Example 5

Immunogenicity and Reactogenicity of Flu ID: Study 2

Preparation of Influenza Virus Antigen Preparation

Monovalent split vaccine was prepared according to the following procedure.

Preparation of Virus Inoculum

On the day of inoculation of embryonated eggs a fresh inoculum was prepared by mixing the working seed lot with a phosphate buffered saline containing gentamycin sulphate at 0.5 mg/ml and hydrocortisone at 25 µg/ml. (virus strain-dependent). The virus inoculum was kept at 2-8° C.

Inoculation of Embryonated Eggs

Nine to eleven day old embryonated eggs were used for virus replication. Shells were decontaminated. The eggs were inoculated with 0.2 ml of the virus inoculum. The inoculated eggs are incubated at the appropriate temperature (virus strain-dependent) for 48 to 96 hours. At the end of the incubation period, the embryos were killed by cooling and the eggs are stored for 12-60 hours at 2-8° C.

Harvest

The allantoic fluid from the chilled embryonated eggs was harvested. Usually, 8 to 10 ml of crude allantoic fluid is collected per egg.

Concentration and Purification of Whole Virus from Allantoic Fluid

1 Clarification

The harvested allantoic fluid was clarified by moderate speed centrifugation (range: 4000-14000 g).

2 Adsorption Step

To obtain a $CaHPO_4$ gel in the clarified virus pool, 0.5 mol/L $Na_2HPO_4$ and 0.5 mol/L $CaCl_2$ solutions were added to reach a final concentration of $CaHPO_4$ of 1.5 g to 3.5 g $CaHPO_4$/liter depending on the virus strain.

After sedimentation for at last 8 hours, the supernatant was removed and the sediment containing the influenza virus was resolubilised by addition of a 0.26 mol/L EDTA-Na$_2$ solution, dependent on the amount of CaHPO$_4$ used.

3 Filtration

The resuspended sediment was filtered on a 6 μm filter membrane.

4 Sucrose Gradient Centrifugation

The influenza virus was concentrated by isopycnic centrifugation in a linear sucrose gradient (0.55% (w/v)) containing 100 μg/ml Thiomersal. The flow rate was 8-15 liters/hour.

At the end of the centrifugation, the content of the rotor was recovered by four different fractions (the sucrose is measured in a refractometer):

fraction 1 55-52% sucrose
fraction 2 approximately 52-38% sucrose
fraction 3 38-20% sucrose*
fraction 4 20-0% sucrose

* virus strain-dependent: fraction 3 can be reduced to 15% sucrose.

For further vaccine preparation, only fractions 2 and 3 are used.

Fraction 3 was washed by diafiltration with phosphate buffer in order to reduce the sucrose content to approximately below 6%. The influenza virus present in this diluted fraction was pelleted to remove soluble contaminants.

The pellet was resuspended and thoroughly mixed to obtain a homogeneous suspension. Fraction 2 and the resuspended pellet of fraction 3 were pooled and phosphate buffer was added to obtain a volume of approximately 40 liters, a volume appropriate for 120,000 eggs/batch. This product was the monovalent whole virus concentrate.

5 Sucrose Gradient Centrifugation with Sodium Deoxycholate

The monovalent whole influenza virus concentrate was applied to a ENI-Mark II ultracentrifuge. The K3 rotor contained a linear sucrose gradient (0.55% (w/v)) where a sodium deoxycholate gradient was additionally overlayed. Tween 80 was present during splitting up to 0.1% (w/v) and Tocopherol succinate was added for B-strain-viruses up to 0.5 mM. The maximal sodium deoxycholate concentration was 0.7-1.5% (w/v) and is strain dependent. The flow rate is 8-15 liters/hour.

At the end of the centrifugation, the content of the rotor was recovered by three different fractions (the sucrose is measured in a refractometer). Fraction 2 was used for further processing. Sucrose content for fraction limits (47-18%) varied according to strains and was fixed after evaluation:

6 Sterile Filtration

The split virus fraction was filtered on filter membranes ending with a 0.2 μm membrane. Phosphate buffer containing 0.025% (w/v) Tween 80 and (for B strain viruses) 0.5 mM Tocopherol succinate was used for dilution. The final volume of the filtered fraction 2 was 5 times the original fraction volume.

7 Inactivation

The filtered monovalent material was incubated at 22±2° C. for at most 84 hours (dependent on the virus strains, this incubation can be shortened). Phosphate buffer containing 0.025% (w/v). Tween 80 was then added in order to reduce the total protein content down to max. 250 μg/ml. For B strain viruses, a phosphate buffered saline containing 0.025% (w/v) Tween 80 and 0.25 mM Tocopherol succinate was applied for dilution to reduce the total protein content down to 250 μg/ml. Formaldehyde was added to a final concentration of 50 μg/ml and the inactivation took place at 20° C.±2° C. for at least 72 hours.

8 Ultrafiltration

The inactivated split virus material was concentrated at least 2 fold in a ultrafiltration unit, equipped with cellulose acetate membranes with 20 kDa MWCO. The material was subsequently washed with phosphate buffer containing 0.025% (w/v) Tween 80 and following with phosphate buffered saline containing 0.01% (w/v) Tween. For B strain virus a phosphate buffered saline containing 0.01% (w/v) Tween 80 and 0.1 mM Tocopherol succinate was used for washing.

9 Final Sterile Filtration

The material after ultrafiltration was filtered on filter membranes ending with a 0.2 μm membrane. Filter membranes were rinsed and the material was diluted if necessary such that the protein concentration does not exceed 1,000 μg/ml but haemagglutinin concentration exceeds 180 μg/ml with phosphate buffered saline containing 0.01% (w/v) Tween 80 and (for B strain viruses) 0.1 mM Tocopherol succinate.

10 Storage

The monovalent final bulk was stored at 2-8° C. for a maximum of 18 months.

Example 6

Preparation of Influenza Vaccine

Monovalent final bulks of three strains, A/New Caledonia/20/99 (H1N1) IVR-116, A/Panama/2007/99 (H3N2) Resvir-17 and B/Johannesburg/5/99 were produced according to the method described in Example 5.

Pooling

The appropriate amount of monovalent final bulks were pooled to a final HA-concentration of 60 μg/ml for A/New Caledonia/20/99 (H1N1) IVR-116, A/Panama/2007/99 (H3N2) Resvir-17, respectively and of 68 μg/ml for B/Johannesburg/5/99. Tween 80, Triton X-100 and Tocopherol succinate were adjusted to 1,000 μg/ml, 110 μg/ml and 160 μg/ml, respectively. The final volume was adjusted to 3 l with phosphate buffered saline. The trivalent pool was filtered ending with 0.8 μm cellulose acetate membrane to obtain the trivalent final bulk. Trivalent final bulk was filled into syringes at least 0.165 mL in each.

Vaccine Administration

The vaccine was supplied in pre-filled syringes and was administered intradermally in the deltoid region. The intradermal (ID) needle was as described in EP1092444, having a skin penetration limiter to ensure proper intradermal injection. Since formation of a wheal (papule) at the injection site demonstrates the good quality of ID administration, the investigator with the subject measured the exact size of the wheal 30 minutes after vaccination.

One dose (100 μl) contained the following components:

| HEMAGGLUTININ FROM THREE INFLUENZA STRAINS | |
|---|---|
| A/NEW CALEDONIA/20/99 | 6.0 μg |
| A/PANAMA/2007/99 | 6.0 μg |
| B/JOHANNESBURG 5/99 | 6.0 μg |
| THIOMERSAL PRESERVATIVE | 0.4 μg-0.8 μg |

The above vaccine was compared a standard trivalent split influenza vaccine: Fluarix™. The Fluarix vaccine was supplied in pre-filled syringes and was administered intramuscularly in the deltoid muscle. A needle of at least 2.5 cm/1 inch in length (23 gauge) was used to ensure proper intramuscular injection.

One dose (0.5 ml) contained the following components

| HEMAGGLUTININ FROM THREE INFLUENZA STRAINS | |
|---|---|
| A/NEW CALEDONIA/20/99 | 15.0 µg |
| A/PANAMA/2007/99 | 15.0 µg |
| B/JOHANNESBURG 5/99 | 15.0 µg |
| THIOMERSAL PRESERVATIVE | 50.0 µg |

Results

The mean age of the total cohort at the time of vaccine administration was 70.4±6.2 years Standard Deviation (S.D.), the female/male ratio was 1.7:1.

Immunogenicity results: Analysis of derived immunogenicity variables was as follows:

| Variable | | Flu-red ID (N = 65) | | | Fluarix ™ IM (N = 65) | | |
|---|---|---|---|---|---|---|---|
| GMT | | GMT | LL | UL | GMT | LL | UL |
| A/NEW CALEDONIA | PRE | 99.5 | 76.9 | 128.7 | 90.0 | 70.1 | 115.7 |
| | POST | 165.1 | 129.2 | 211.0 | 174.3 | 133.3 | 227.9 |
| A/PANAMA | PRE | 75.5 | 54.7 | 104.2 | 69.2 | 51.9 | 92.4 |
| | POST | 128.6 | 99.1 | 166.8 | 164.3 | 126.0 | 214.1 |
| B/ JOHANNESBURG | PRE | 236.0 | 187.7 | 296.8 | 222.6 | 176.9 | 280.2 |
| | POST | 341.2 | 276.0 | 421.7 | 402.4 | 312.1 | 518.9 |
| Seroconversion rate | | % | LL | UL | % | LL | UL |
| A/NEW CALEDONIA | | 15.4 | 7.6 | 26.5 | 18.5 | 9.9 | 30.0 |
| A/PANAMA | | 20.0 | 11.1 | 31.8 | 29.2 | 18.6 | 41.8 |
| B/ JOHANNESBURG | | 9.2 | 3.5 | 19.0 | 16.9 | 8.8 | 28.3 |
| Conversion factor | | GMR | LL | UL | GMR | LL | UL |
| A/NEW CALEDONIA | | 1.7 | 1.4 | 2.0 | 1.9 | 1.6 | 2.3 |
| A/PANAMA | | 1.7 | 1.4 | 2.1 | 2.4 | 1.9 | 3.0 |
| B/ JOHANNESBURG | | 1.4 | 1.2 | 1.7 | 1.8 | 1.5 | 2.1 |
| Seroprotection rate | | % | LL | UL | % | LL | UL |
| A/NEW CALEDONIA | PRE | 87.7 | 77.2 | 94.5 | 90.8 | 81.0 | 96.5 |
| | POST | 92.3 | 83.0 | 97.5 | 96.9 | 89.3 | 99.6 |
| A/PANAMA | PRE | 75.4 | 63.1 | 85.2 | 81.5 | 70.0 | 90.1 |
| | POST | 90.8 | 81.0 | 96.5 | 93.8 | 85.0 | 98.3 |
| B/ JOHANNESBURG | PRE | 98.5 | 91.7 | 100.0 | 96.9 | 89.3 | 99.6 |
| | POST | 100.0 | 94.5 | 100.0 | 98.5 | 91.7 | 100.0 |

N: number of subjects with available results;
%: percentage of subjects within the given parameter;
LL/UL: lower and upper limit of 95% CI;
Pre: at the time of vaccine administration;
Post: 21 days after the vaccine dose Injection site pain, reported by 10/65 (15.4%) vaccinees, was the most common symptom following IM administration of Fluarix™. In the ID group, pain was reported by 3/65 (4.6%) vaccinees. This difference was statistically significant (p=0.038; Fisher exact test). Frequency of pain is therefore reduced when using ID administration.

Conclusions

ID administration of a flu vaccine provides equivalent (100%) seroprotection in an elderly population.

A comparable response to vaccination in terms of geometric mean titers, seroprotection rates, seroconversion rates and conversion factors was found in IM and ID vaccinated individuals where the ID group received 2.5-fold less antigen.

There was no discernible difference in the overall incidence of vaccine-related solicited/unsolicited systemic symptoms in the two treatment groups.

Example 7

Intradermal Delivery Using Standard Needle

Immunogenicity of the split influenza vaccine was assessed by ID delivery in pigs using a standard needle.

Pigs show important physiologic similarities to humans, and pig skin in particular is quite similar to human skin in terms of appearance, anatomy, and physiology. Therefore, studies where properties of the skin are important may be assessed in the most relevant manner in pigs. The pig also has the advantage that it is a natural host for influenza infection (A strains only) and thus testing of vaccine candidates in pigs is relevant.

In a first immunogenicity study conducted in 4 week old pigs, 3 groups of 6 pigs each were primed by intranasal administration of whole, inactivated, trivalent influenza (50 µg each HA adjuvanted with 0.5% Laureth 9) in a total volume of 200 µl-100 µl administered in each nostril using a Pfeiffer intranasal device (described for example in WO 91/13281, EP 311 863 B and EP 516 636 B, commercially available from Pfeiffer GmbH). A second priming dose was administered at day 11.

On day 39 the animals were vaccinated by either the ID (Fluarix™ or PBS control) or IM (Fluarix™ only) route. Animals receiving IM vaccination were immunized with trivalent Fluarix™ (15 µg each HA of strains A/New Caledonia H1N1, A/Panama H3N2, and B/Johannesburg) in 0.5 ml administered in the front leg. Animals receiving ID vaccination were immunized with trivalent Fluarix™ (3 µg each HA) or PBS in 0.1 ml administered using a standard needle.

Blood samples were obtained on day 53 and tested for anti-influenza activity using ELISA assays.

The results of this first immunogenicity study are presented in FIG. 1 which shows the results obtained from this study using the strain-specific ELISA readout.

Legend to FIG. 1:
Group 1: 2 IN Primings (Trivalent 50 µg); trivalent vaccine IM 15 µg HA
Group 2: 2 IN Primings (Trivalent 50 µg); trivalent vaccine ID 3 µg HA
Group 3: 2 IN Primings (Trivalent 50 µg); PBS ID The results confirm the immunogenicity of the trivalent influenza vaccine administered to primed pigs by either the IM or ID route.

Example 8

Intradermal Delivery of Adjuvanted Influenza Vaccine

Protocol

Guinea pigs were primed on Day 0 with 5 µg trivalent whole inactivated Flu virus in 200 µl, intranasally.

Vaccination—Day 28—Vaccine containing 0.1 µg HA each per strain trivalent split Flu vaccine prepared as described in Examples 5 and 6 except that the pooling (Example 6) resulted in a final concentration for each antigen of 1.0 µg/ml to give a dose of 0.1 µg in 100 µl compared to 60 µg/ml in Example 6. The final trivalent formulation was administered intradermally using tuberculin syringes, either adjuvanted or unadjuvanted, in 100 μl.

Bleeding—Day 42.

The effect of adjuvantation was assessed by measuring antibody responses by HI assay (day 0, 28, 42).

All ID experiments were carried out using a standard needle.

Results

G1-G5 refer to 5 groups of guinea pigs, 5 per group.
G1 Split trivalent thiomersal reduced 0.1 μg
G2 Split trivalent thio red 0.1 μg+3D-MPL 50 μg
G3 Split trivalent thio red 0.1 μg+3D-MPL 10 μg
G4 Split trivalent thio red 0.1 μg+3D-MPLin 50 μg+QS21 50 μg
G5 Split trivalent thio red 0.1 μg+3D-MPLin 10 μg+QS21 10 μg Note 3D-MPLin+QS21 refers to an adjuvant formulation which comprises a unilamellar vesicle comprising cholesterol, having a lipid bilayer comprising dioleoyl phosphatidyl choline, wherein the QS21 and the 3D-MPL are associated with, or embedded within, the lipid bilayer. Such adjuvant formulations are described in EP 0 822 831 B, the disclosure of which is incorporated herein by reference.

HI Titres Anti-A/New Caledonia/20/99

| NC | Pre-immun | Pre-boost | Post-boost |
|---|---|---|---|
| G1 | 5 | 10 | 92 |
| G2 | 5 | 10 | 70 |
| G3 | 5 | 11 | 121 |
| G4 | 7 | 9 | 368 |
| G5 | 5 | 10 | 243 |

HI Titres Anti-A/Panama/2007/99

| P | Pre-immun | Pre-boost | Post-boost |
|---|---|---|---|
| G1 | 5 | 485 | 7760 |
| G2 | 5 | 279 | 7760 |
| G3 | 5 | 485 | 8914 |
| G4 | 7 | 485 | 47051 |
| G5 | 5 | 320 | 17829 |

HI Titres Anti-B/Johannesburg/5/99

| J | Pre-immun | Pre-boost | Post-boost |
|---|---|---|---|
| G1 | 5 | 23 | 184 |
| G2 | 5 | 11 | 121 |
| G3 | 5 | 11 | 70 |
| G4 | 6 | 15 | 557 |
| G5 | 5 | 13 | 320 |

The data presented in this example confirm and extend the results obtained in the previous example, conducted in pigs. ID administration of trivalent Flu vaccine induces a strong immune response in primed animals (guinea pigs in addition to pigs). In addition, the potential for adjuvants to further boost this immune response is exemplified. Two different doses of 3D-MPLin+QS21 were shown to significantly boost the antibody titres induced by vaccination with unadjuvanted split trivalent Flu antigen. Thus, a Flu ID vaccine can be successfully adjuvanted and the resulting product can induce enhanced immune responses in vaccinated individuals.

We claim:

1. A method for vaccinating an individual selected from a human population of at least 18 years of age, the method comprising administering intradermally to said individual a single dose of a trivalent, split or subunit influenza vaccine antigen preparation, using a short needle device wherein the vaccine is provided in a dose volume of between about 0.05 and about 0.2 ml and wherein the vaccine induces a protective immune response in the human population of at least 18 years of age, wherein said protective immune response meets at least one criterion chosen from the group of:
    (1) a protection rate of >70% in adults of 18-60 years of age or of >60% in elderly people of above 60 years of age;
    (2) a seroconversion rate of >40% in adults of 18-60 years of age or of >30% in elderly people of above 60 years of age; or
    (3) a conversion factor of >2.5 HI titres in adults of 18-60 years of age or of >2.0 HI titres in elderly people of above 60 years of age, for each influenza strain.

2. The method according to claim 1, wherein the influenza antigen is egg-derived.

3. The method according claim 1, wherein the vaccine further comprises an adjuvant comprising a combination of cholesterol, a saponin and an LPS derivative.

4. The method according to claim 1, wherein said influenza vaccine antigen preparation is obtained by a process comprising: (i) harvesting virus-containing material from a culture; (ii) clarifying the harvested material to remove non-virus material; (iii) concentrating the harvested virus; (iv) separating whole virus from non-virus material; (v) splitting the whole virus using a suitable splitting agent in a density gradient centrifugation step; and (vi) filtering the product of step (v) to remove undesired materials.

5. The method according to claim 1, wherein the vaccine antigen preparation is a trivalent, split influenza vaccine antigen preparation.

6. The method according to claim 1, wherein the vaccine antigen preparation is a trivalent, subunit influenza vaccine antigen preparation.

7. The method according to claim 1, wherein said protective immune response meets at least two criteria chosen from the group of: (1) a protection rate of >70% in adults of 18-60 years of age or of >60% in elderly people of above 60 years of age; (2) a seroconversion rate of >40% in adults of 18-60 years of age or of >30% in elderly people of above 60 years of age; or (3) a conversion factor of >2.5 HI titres in adults of 18-60 years of age or of >2.0 HI titres in elderly people of above 60 years of age, for each influenza strain.

8. The method according to claim 7, wherein the influenza antigen is egg-derived.

9. The method according to claim 7, wherein the vaccine is provided in a dose volume of between about 0.1 and about 0.2 ml.

10. The method according to claim 7, wherein the vaccine further comprises an adjuvant comprising a combination of cholesterol, a saponin and an LPS derivative.

11. The method according to claim 7, wherein the vaccine antigen preparation is a trivalent, split influenza vaccine antigen preparation.

12. The method according to claim 7, wherein the vaccine antigen preparation is a trivalent, subunit influenza vaccine antigen preparation.

13. The method according to claim 7, wherein said influenza vaccine antigen preparation is obtained by a process comprising: (i) harvesting virus-containing material from a culture; (ii) clarifying the harvested material to remove non-virus material; (iii) concentrating the harvested virus; (iv)

separating whole virus from non-virus material, (v) splitting the whole virus using a suitable splitting agent in a density gradient centrifugation step; and (vi) filtering the product of step (v) to remove undesired materials.

14. The method according to claim 1, wherein said protective immune response meets all three criteria chosen from the group of (1) a protection rate of >70% in adults of 18-60 years of age or of >60% in elderly people of above 60 years of age; (2) a seroconversion rate of >40% in adults of 18-60 years of age or of >30% in elderly people of above 60 years of age; and (3) a conversion factor of >2.5 HI titres in adults of 18-60 years of age or of >2.0 HI titres in elderly people of above 60 years of age, for each influenza strain.

15. The method according to claim 14, wherein the influenza antigen is egg-derived.

16. The method according to claim 14, wherein the vaccine is provided in a dose volume of between about 0.1 and about 0.2 ml.

17. The method according to claim 14, wherein the vaccine antigen preparation is a trivalent, split influenza vaccine antigen preparation.

18. The method according to claim 14, wherein the vaccine antigen preparation is a trivalent, subunit influenza vaccine antigen preparation.

19. The method according claim 14, wherein the vaccine further comprises an adjuvant comprising a combination of cholesterol, a saponin and an LPS derivative.

20. The method according to claim 14, wherein said influenza vaccine antigen preparation is obtained by a process comprising, (i) harvesting virus-containing material from a culture; (ii) clarifying the harvested material to remove non-viral material; (iii) concentrating the harvested virus; (iv) separating whole virus from non-virus material; (v) splitting the whole virus using a suitable splitting agent in a density gradient centrifugation step; and (vi) filtering the product of step (v) to remove undesired materials.

* * * * *